US00PP23930P3

(12) United States Plant Patent
Rohde

(10) Patent No.: US PP23,930 P3
(45) Date of Patent: Sep. 24, 2013

(54) ***SCHLUMBERGERA* PLANT NAMED 'SAO PAULO BRAZIL'**

(50) Latin Name: *Schlumbergera truncata hybr.*
Varietal Denomination: Sao Paulo Brazil

(75) Inventor: Frank Rohde, Kerteminde (DK)

(73) Assignee: Rohdes A/S, Kerteminde (DK)

( * ) Notice: Subject to any disclaimer, the term of this patent is extended or adjusted under 35 U.S.C. 154(b) by 357 days.

(21) Appl. No.: 13/064,060

(22) Filed: Mar. 3, 2011

(65) Prior Publication Data

US 2012/0227149 P1 Sep. 6, 2012

(51) Int. Cl.
*A01H 5/00* (2006.01)

(52) U.S. Cl.
USPC ..... Plt./372

(58) Field of Classification Search
USPC ..... Plt./372
See application file for complete search history.

(56) References Cited

U.S. PATENT DOCUMENTS

PP22,085 P3 * 8/2011 Boyle et al. ..... Plt./372

OTHER PUBLICATIONS upov pluto Citations for 'Sao Paulo Brazil'.*

Application information from Community Plant Variety Office (CPVO) website for corresponding CPVO application No. 2010/0057 filed Jan. 11, 2010 (1 page) (http://www.cpvoextranet.cpvo.europa.eu).

* cited by examiner

*Primary Examiner* — Wendy C Haas

(74) *Attorney, Agent, or Firm* — Foley & Lardner LLP

(57) ABSTRACT

A new and distinct cultivar of *Schlumbergera* plant named 'Sao Paulo Brazil', characterized by its pure white colored flowers; dense and bushy plant form; and moderate growth habit.

3 Drawing Sheets

Latin name of the genus and species claimed: *Schlumbergera truncata hybr.*

Variety denomination: 'SAO PAULO BRAZIL'.

BACKGROUND OF THE INVENTION

The present invention relates to a new and distinct cultivar of *Schlumbergera* plant, botanically known as *Schlumbergera truncata hybr.*, common name Thanksgiving Cactus, and hereinafter referred to by the variety denomination 'Sao Paulo Brazil'.

The new *Schlumbergera* is a product of a planned breeding program conducted by the inventor, Frank Rohde, in Fyn, Denmark. The new *Schlumbergera* originated from an outcrossing made in 2007 by the Inventor between two proprietary cultivars of *Schlumbergera truncata hybr.* The female or seed parent is the *Schlumbergera truncata hybr.* variety designated 'Jolly Dancer' (unpatented). The male or pollen parent is the proprietary *Schlumbergera truncata hybr.* variety designated 3666 C (unpatented). The Inventor selected the new *Schlumbergera* cultivar from the progeny of the above crossing in 2008 on the basis of its flower color and fairly compact, freely branching habit. Plants of the new *Schlumbergera* are more upright, and have a unique color combination of the flowers combined with healthy, shiny dark green phyllocladia and excellent branching.

Asexual reproduction of the new cultivar by phyllocladia cuttings taken and propagated and trial production batches in Fyn, Denmark, has shown that the unique features of this new *Schlumbergera* are stable and reproduced true to type in many successive generations.

BRIEF DESCRIPTION OF THE INVENTION

The following traits have been repeatedly observed and are determined to be the unique characteristics of 'Sao Paulo'. These characteristics in combination distinguish 'Sao Paulo' as a new and distinct cultivar:

1. Pure white flowers;
2. Large upright to vertical flowers with less reflexing of petals;
3. Moderately vigorous growth habit;
4. Higher number of flowers per plant;
5. White buds, ovoid to lanceolatoid in shape.

Plants of the cultivar 'Sao Paulo' can be compared to plants of the *Schlumbergera truncata hybr.* cultivar 'Malissa' (unpatented). However, in side-by-side comparisons conducted over several seasons by the inventor in Hundslev, Denmark, plants of the cultivar 'Sao Paulo Brazil' and the cultivar 'Malissa' differ in the following characteristics:

1. Plants of the new *Schlumbergera* have larger flowers than plants of the cultivar 'Malissa'.
2. Plants of the new *Schlumbergera* have less reflexing petals than plants of the cultivar 'Malissa'.
3. Plants of the new *Schlumbergera* have longer and darker green (RHS 137A) phyllocladia than plants of the cultivar 'Malissa' (RHS 137B).
4. Plants of the new *Schlumbergera* have more serrated phyllocladia compared to 'Malissa'.
5. Plants of the new *Schlumbergera* are taller than the plants of the cultivar 'Malissa'
6. Plants of the new *Schlumbergera* have more flowers per plant than the plants of the cultivar 'Malissa'

BRIEF DESCRIPTION OF THE DRAWINGS

The accompanying colored photographs illustrate the overall appearance and details of flower form color and structures of the new cultivar, showing the colors as true as it is reasonably possible to obtain in colored reproductions of this type. Colors in the photographs may differ slightly from the color values cited in the detailed botanical description, which more accurately describe the actual colors of the claimed variety.

DETAILED BOTANICAL DESCRIPTION

Figure 1:
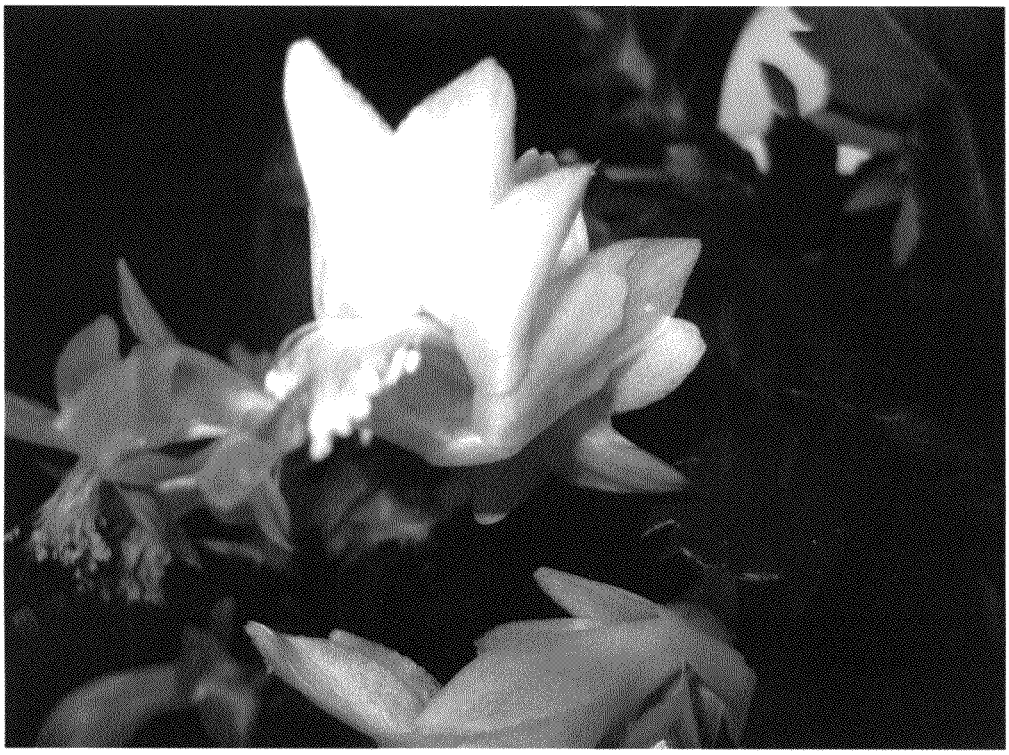
FIG. 1—shows a close up view of a single flower and a large bud of 'Sao Paulo Brazil'.
Figure 2:
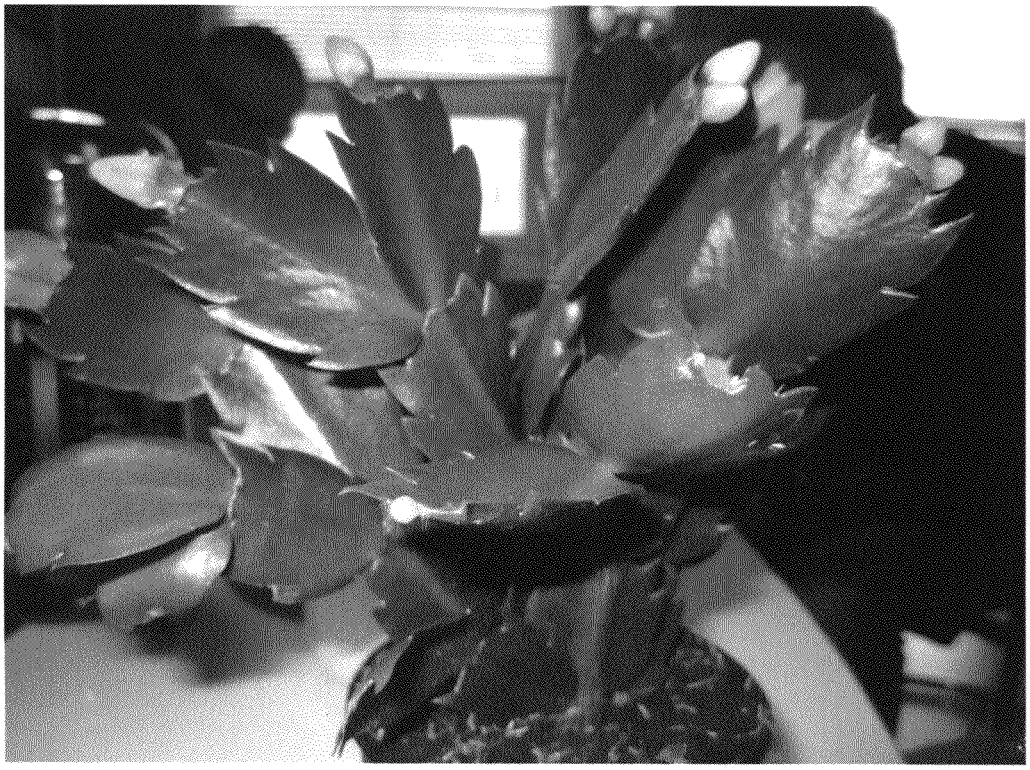
FIG. 2—shows a side/top view of a budding plant of 'Sao Paulo Brazil'.
Figure 3:
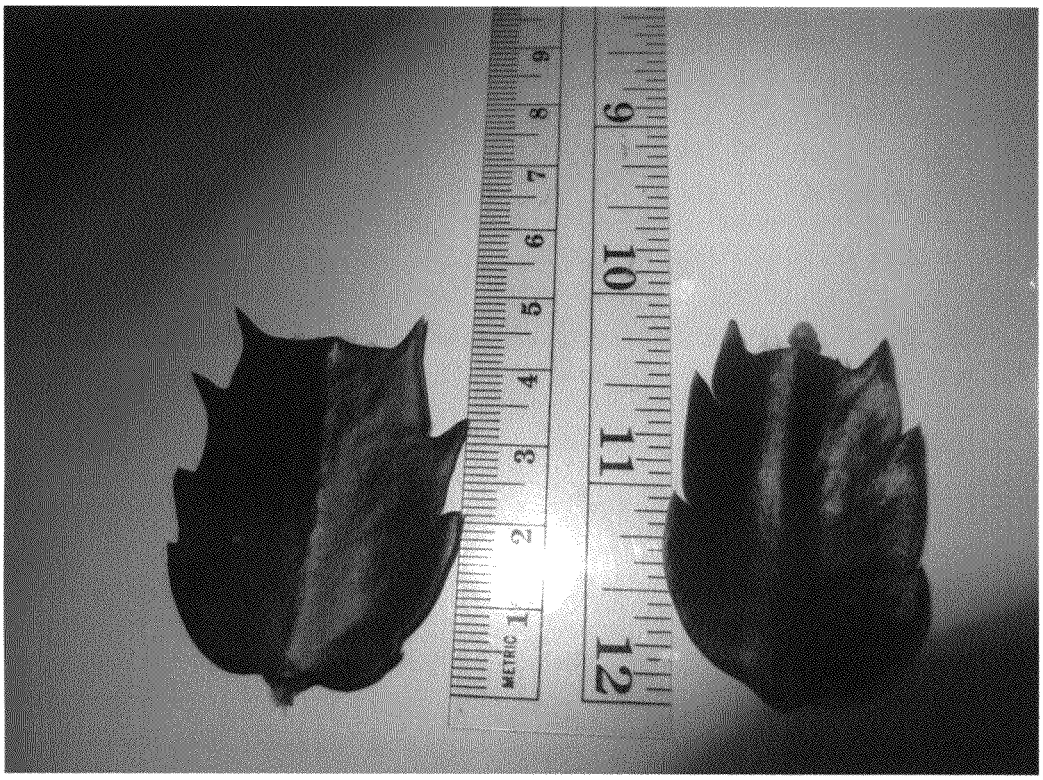
FIG. 3—shows the size and shape of typical phyllocladia of 'Sao Paulo Brazil'.

Plants of the cultivar 'Sao Paulo Brazil' have not been observed under all possible environmental conditions. The phenotype may vary somewhat with variations in environment such as temperature, light intensity, day length, and fertility level without, however, any variance in genotype.

In the following description, color references are made to The Royal Horticultural Society Colour Chart, 4$^{th}$ edition, where general terms of ordinary dictionary significance are used. Plants were grown under greenhouse conditions. Plants used for this description were grown for about 40 weeks after cutting.

Classification:

*Botanical.*—*Schlumbergera truncata hybr.*

*Variety denomination.*—'Sao Paulo Brazil'.

Parentage:

*Female or seed parent.*—*Schlumbergera truncata hybr.* 'Jolly Dancer' (unpatented).

*Male or pollen parent.*—*Schlumbergera truncata hybr.* Unnamed, non-patented cultivar (3666 A).

Propagation:

*Type cutting.*—Single mature phyllocladia.

*Time to initiate roots.*—About 30 days at 18 to 21 C in a greenhouse.

*Root description.*—Fine, well branched.

*Plant description.*—Form.— Perennial plant (epiphyte), young plants have an upright plant habit. *Schlumbergera* flowers singular or double (seldom triple) at apical ends of terminal phyllocladia. Freely branching with two or three new phyllocladia forming at the apical ends of older phyllocladia. Crop time.— After rooting, about 10 months are required to produce finished flowering plants in 9 cm pots.

Plant:

*Plant height* (*soil level to top of plant, incl. flowers*).—About 14 cm.

*Vigor.*—Slow growth rate.

*Foliage.*—Length: 4 to 5 cm. Width: 3 to 3.5 cm, Margin: slightly serrated. Texture: glabrous. Branching: once or twice. Shape: Oval, with truncate tips ending in 2 marginal protruding teeth 8 to 9 mm long, forming a claw-like shape. Edges: sparsely dentate with 6 to 7 mm long teeth. Venation: costate. Thickness (at the center vein): 4-5 mm. Color: green (RHS 137A-C). Apex: Barbellate with 5 to 7 short stiff hairs, but no true areole structures.

Infloresence:

*Blooming season.*—October to January in the Northern hemisphere.

*Longevity on plant.*—Highly dependent on temperature and light conditions; generally 5 to 6 days. Flowers are persistent with petals folding and withering slowly.

*Buds.*—Aspect: upright. Length: 4.5 cm. Diameter: 10 mm diameter. Shape: lanceolatoid to ovoid, (globular). Color: RHS 145D, Light green, to RHS N155A, white.

*Flowers.*—Arrangement: Single or double sessile flowers on apical phyllocladia. Shape: tubular, zygomorphic and at right angles to the phyllocladium when mature. During development perianth lobes may become reflexed or refracted (more pronounced). Diameter: 8 to 10 cm. Height: 7 cm. Petal Color: Upper surfaces, lobe edges RHS N155A, white with stripes and throat turning to RHS 76D light purple if temperatures during development are low (i.e., less than 18 degrees C.).

*Stamen.*—Number: many, polyandrous, Shape: incurved. Some filaments fused to perianth tube (connate). Color: translucent white — RHS 155D. Length: 65 to 70 mm.

*Anther.*—Shape: ovoid. Color: RHS 11C, light yellow. Length: 1 mm.

*Pistil and stigma.*—Length: 60 mm. Shape: slightly curved. Stigma has claw-like shape. Color RHS N74A, purple.

*Ovary.*—Length: 4-5 mm long, Shape: angular. Color: RHS 144A, yellow green.

Seeds: None observed.

Weather tolerance: Good tolerance to drought.

What is claimed is:

1. A new and distinct cultivar of *Schlumbergera* plant named 'Sao Paulo Brazil', as illustrated and described herein.

* * * * *